United States Patent
Kunz et al.

(10) Patent No.: US 9,596,030 B2
(45) Date of Patent: Mar. 14, 2017

(54) INNOVATIVE OPERATION ROOM LIGHT SYSTEM CAPABLE OF WIRELESS DATA EXCHANGE BETWEEN OPERATING ROOM DEVICES

(71) Applicants: Reiner Kunz, Kleinmachnow (DE); Michael Schmidt, Halifax (CA)

(72) Inventors: Reiner Kunz, Kleinmachnow (DE); Michael Schmidt, Halifax (CA)

(*) Notice: Subject to any disclaimer, the term of this patent is extended or adjusted under 35 U.S.C. 154(b) by 0 days.

(21) Appl. No.: 15/038,674

(22) PCT Filed: Nov. 25, 2014

(86) PCT No.: PCT/EP2014/075592
§ 371 (c)(1),
(2) Date: May 23, 2016

(87) PCT Pub. No.: WO2015/075276
PCT Pub. Date: May 28, 2015

(65) Prior Publication Data
US 2016/0301471 A1   Oct. 13, 2016

(30) Foreign Application Priority Data
Nov. 25, 2013  (DE) .................. 10 2013 113 023

(51) Int. Cl.
*H04B 10/50*     (2013.01)
*H04B 10/58*     (2013.01)
(Continued)

(52) U.S. Cl.
CPC ............ *H04B 10/116* (2013.01); *A61B 90/30* (2016.02); *G08C 23/04* (2013.01);
(Continued)

(58) Field of Classification Search
CPC .... H04B 10/58; H04B 10/116; H04B 10/503; H04B 10/1143; A61B 90/30; G08C 23/04
(Continued)

(56) References Cited

U.S. PATENT DOCUMENTS

2006/0140139 A1* 6/2006 DiSilvestro .......... A61B 5/0028
                                                                     370/310
2011/0015492 A1   1/2011 Mangiardi
(Continued)

FOREIGN PATENT DOCUMENTS

| DE | 19653507 A1 | 6/1998 |
| DE | 102008012824 A1 | 9/2009 |
| EP | 1785965 A2 | 5/2007 |

OTHER PUBLICATIONS

International Search Report and Written Opinion dated Apr. 8, 2016, in International Application No. PCT/EP2014/075592.

*Primary Examiner* — Dalzid Singh
(74) *Attorney, Agent, or Firm* — Downs Rachlin Martin PLLC

(57) ABSTRACT

The invention relates to a communication system and devices forming part of this system, wherein light is used for the transmission signal. The communication system includes an apparatus for forwarding operating room device signals to a device which apparatus is configured to receive an analog signal comprising the operating room device signal and to produce a digital signal based upon the analog signal, the apparatus further being configured to produce a signal based upon the digital signal, wherein the signal is for modulating the output of a light source. This invention includes a device for managing access and priority of traffic within this system according to a specific hierarchy of priority starting with safety and ending with administrative information.

19 Claims, 3 Drawing Sheets

(51) Int. Cl.
*H04B 10/114* (2013.01)
*H04B 10/116* (2013.01)
*G08C 23/04* (2006.01)
*A61B 90/30* (2016.01)

(52) U.S. Cl.
CPC ....... *H04B 10/1143* (2013.01); *H04B 10/503* (2013.01); *H04B 10/58* (2013.01); *A61B 2090/309* (2016.02)

(58) Field of Classification Search
USPC .......................................................... 398/118
See application file for complete search history.

(56) References Cited

U.S. PATENT DOCUMENTS

| | | | | |
|---|---|---|---|---|
| 2012/0161647 | A1* | 6/2012 | Fornasiero | H05B 33/0857 315/158 |
| 2014/0159856 | A1* | 6/2014 | Meyer | G05B 23/0221 340/5.1 |
| 2015/0141751 | A1* | 5/2015 | Finkman | A61B 1/00013 600/109 |

* cited by examiner

INNOVATIVE OPERATION ROOM LIGHT SYSTEM CAPABLE OF WIRELESS DATA EXCHANGE BETWEEN OPERATING ROOM DEVICES

FIELD OF THE INVENTION

The application relates to data transfer and, in particular, to an operating room device such as but not restricted to a surgical lamp capable of forwarding and receiving signals to and from other operating room devices using light.

BACKGROUND OF THE INVENTION

In visible light communication systems, data signals are modulated into visible light. At practical data rates, the modulation is too rapid to be sensed by the human eye. The visible light can thus be used for both illumination and communication. Light emitting diodes (LEDs) are often used as the light source because, amongst other things, their output can be modulated sufficiently rapidly.

The use of white LEDs for illumination is also becoming increasingly widespread.

US 2011/0069958 A1 discloses an aircraft data communication system using optical wireless data transmission. The light is non-coherent infrared light.

A communication apparatus for forwarding a mobile telephony signal to a mobile device and a communication system using light are subject of WO 2013/114103 A1. US 2012/0134433 A1 and US 2012/0044846 A1 are related to communication systems allowing efficient transmission and energy reduction.

Nevertheless, many ways of exploiting the potential of visible light communications and of implementing practical systems remain unexplored.

DE 20 2013 006 570 U1 describes a surgical lamp wherein LEDs are used and the colour temperature of the emitted radiation can be varied between 3.500 and 5.500 K. As well, the radiation intensity can be varied.

Another conventional surgical LED lamp is shown in FIG. 1.

DE 10 2008 012 824 A1 describes a further surgical lamp comprising a signal light source emitting light that may be modulated so that it includes information for transmission to the surgical area and to a surgical instrument. The surgical instrument, on the other hand, may be equipped with means for transmitting information such as measurement values to the surgical lamp.

Use of WLAN and WiFi in the field of medicine involves problems with respect to security. These include disturbances because of frequencies overlapping with those of other equipment that may result in undesired signal/noise ratios up to cutting the connections. Apart therefrom other problems are caused by the requirement of fast data transmission not being met by WLAN and WiFi networks. Further the security of the signals and the possibility of WiFi and WLAN penetrating the walls and the signal being available outside of the operation room, or of signals entering the operation room from outside of the operation room are unacceptable risks.

Further there are many risks introduced into the operation room setting with the encumbrance of cables and multiple cables per operation room device in the room. Cables pose both a physical risk to the patient and to the medical personnel who must carefully work around them. They impede movement and ease of function as well as act as vectors for transmitting infection and disease. It is very difficult to sterilize cables and connectors. It is very easy to trip over them.

SUMMARY OF THE INVENTION

According to a first aspect of the invention, an operation room system includes at least a first device and a second device, wherein the first device is provided with means for emitting and for receiving light signals and the second device is provided with means for receiving and emitting light signals. The light signals are transferred in an exclusively wireless manner between the first device to the second device and carry information which information is modulated on the light signals. The first device is a lighting device. The second device is a medical instrument, in particular, but not exclusively a minimally invasive instrument, wherein the first device exclusively transfers the control signals of the second device to the second device and wherein all output information from the second device is transferred by means of light signals in a wireless manner to the first device. Control means are provided in the operating room system for managing communication access between the two devices including a hierarchy priority decision means for the data exchange between the first device and the second device.

The medical instrument may be e.g. an endoscope which can be controlled by means of eye-tracking. The control signals are entered into the endoscope via the respective usual devices. However, in the present case of the direct communication may be effected using the surgical lamp and the lighting device, e.g. an overhead lighting device. As can be seen in the following, other devices of the operation room system may serve for transmitting signals, as well. Since all communication is effected wireless, only minimum connections between the instruments and devices of the operation room system have to be provided.

According to a second aspect of the invention further devices may be provided with means for emitting and for receiving light signals carrying information which information is modulated on the light signals, respectively. In this case the communication managing control means includes means for adjusting the bandwidth for communication between each two devices exchanging light signals. The hierarchy priority decision means for the data exchange between the devices is provided with a decision means deciding on the respective communication access of two devices and includes switching means for switching the communication access to the devices with the highest priority.

Further this device adjusts the signals sent and received from all other devices to detect and improve quality reducing jitter and other communication impurities that otherwise cause the signals to be of poor quality.

Thus, data are exchanged in an operating room setting in form of but not restricted to an operating room light. In case of more than two devices communicating with each other the communication may involve the said first device. However, it is also possible that e.g. a third and a fourth device communicate with each other, e.g. the medical instrument and display means receiving image data. The devices may be configured to send and receive an analog signal from and to other operating room devices. Typical examples of such devices might be e.g. patient monitors monitoring and storing vital data such as heart rate, blood-pressure oxygensaturation, monitors displaying X-ray/MRI/CT radiologic data, patient related chart/history data, laboratory results, electrocardiograms, neuro-navigation systems, endoscopic devices and related video signals and data for steering these devices, the anesthesia ventilator monitoring and storing patient related data, electro-cautery and related steering data and video data related to intubation and ventilation of the patient.

The operating room light—in the following OR light—is further configured to produce light for the illumination of the room. In one configuration it produces a continuous phase modulated signal based upon a digital signal, wherein the continuous phase modulated signal is for modulating the output of a light source.

Thus, the operation room system can enable an OR device to receive a signal (such as but not limited to a video signal) and vice versa by a means other than a radio signal. This can be particularly useful for transmission of signals in an OR where the radio signal may be unwanted due to e.g. patient data safety considerations and where artificial lighting may be needed in any case. Furthermore, the OR device signal can be forwarded effectively and efficiently and in way which enables the other device to process the signal in substantially the same way as a received radio signal. As used herein, the term light is used to mean, for example, visible light.

The OR device signal may comprise signals related to but not restricted to video signals and/or eye-tracking system data signals.

The OR lamp may further comprise the light source, the light source may comprise a light emitting diode or a laser diode, and the continuous modulated signal may be used to modulate the intensity of the light emitted by the light emitting diode or laser diode. The light emitting or laser diode may be provided in an array comprising one or more light emitting diodes configured to produce white light.

The devices may be configured to receive a further light signal comprising a further OR device signal from each of one or more OR devices. They may be configured to produce an analog signal based upon the further light signal, wherein the further analog signal is for steering processes in an OR network. The further light signal may have different wavelengths from the light output by the light source.

Thus, the operation room system can also enable OR devices to transmit signals to a network base station by means other than radio signals and to do so in such a way that interference between the transmitted and received light signals is minimized.

According to a further aspect of the invention, there is provided a device for receiving an OR device signal transmitted using light, the device configured to detect and send a light signal comprising the OR device signal and to produce a signal based upon the light signal, wherein the light signal is modulated such that the signal comprises a continuous phase modulated signal, the apparatus further configured to demodulate the signal, to produce a digital signal based upon the demodulated signal, and to produce an analog signal based upon the digital signal, wherein the analog signal is for processing by an OR device in substantially the same way as a received radio signal comprising an electromagnetic signal. Thus, in short the said device is able to process an analog signal from e.g. input measurement signals and to transmit it solely or combined with other signals, and the device is able to produce an analog signal from the received digital signal and to transmit it for e.g. steering purposes to an instrument, etc.

The light may be visible light or infrared light.

The light output by the light source may have different wavelengths from the light signal, which the devices are configured to detect.

The OR device may be configured to receive and send a further analog signal comprising a further OR device signal, to produce a further digital signal based upon the further analog signal. Thus, the devices can e.g. handle signals from instruments issuing analog signals and then issue digital signals for the operation room, and vice versa.

From the above it can be seen that according to another aspect of the invention light comprising the operating room device signal is detected in the operation room system. According to the respective requirements an analog signal based upon the digital signal can be produced, wherein the analog signal is for processing by a device.

Furthermore, a further analog signal comprising a further operating room device signal may be received by a device of the operating room system. A further digital signal based upon the further analog signal is then produced. Based upon this further digital signal a further continuous phase modulated signal may be produced, wherein the further continuous phase modulated signal is for modulating the output of a light source.

Another aspect of the invention includes the provision of segmentation and routing of the traffic to and from devices according to a series of predetermined access and traffic routing business rules. For example all devices accessing the wireless, light based network will have their access and bandwith provided according to a prioritization and guaranteed access device. A device used to monitor activity would not be given the same access as a device actively providing care to the patient. Administrative and information devices would be provided access and bandwidth only after all other needs were met. This traffic management and shaping device increases dramatically the safety of the technology in the OR room.

There may be provided an OR device network comprising several devices according to the second aspect of the invention. There may be provided a communication system comprising an operation room system according to the first aspect of the invention and at least one more of the OR devices, wherein the operation room system includes devices configured to forward the OR device signals to the other OR device using light and the at least one more OR device is configured to transmit the further OR device signal to the operation room system device using further light sources having different wavelengths of the light spectrum used.

As the primary and initial use of this technology is medical in nature, the digital traffic control processing includes technology that discerns the differences in light source communication of data and alters the Bandwidth (the rate at which traffic is transmitted and received between devices and on the network), Latency (the delay in data transmission from source to destination), Jitter (the variation in Latency) and Reliability (the percentage of packets discarded between the source and the destination). It also includes a light communication specific admission control and traffic control processor. This regulates which devices may send and receive data within the light communications network as well and regulating the data flow and prioritizing it within the light communication network.

The light signals from the LED light source are transmitted from an instrument, device, or router to a receiver which may include an OR Lamp or other lighting device.

This device includes the traffic control processor. It will apply its admission control and traffic control policies and then forward the signal to another instrument, device or computer within the room.

DESCRIPTION IF THE DRAWINGS

DESCRIPTION OF EXEMPLARY EMBODIMENT

Figure 1:
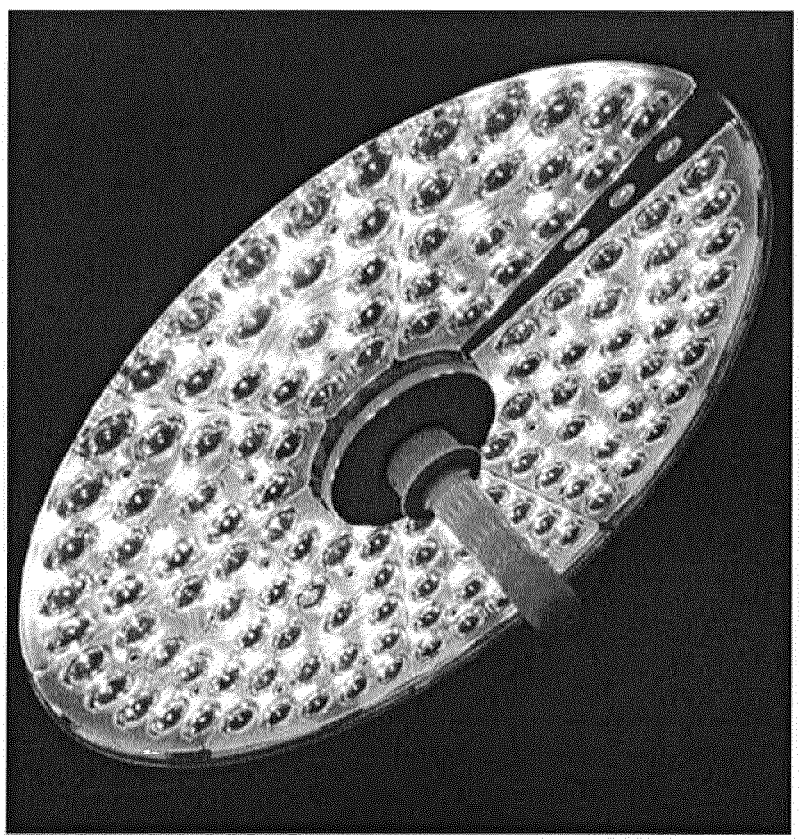
FIG. 1 shows a conventional surgical OR light equipped with LEDs.
Figure 2:
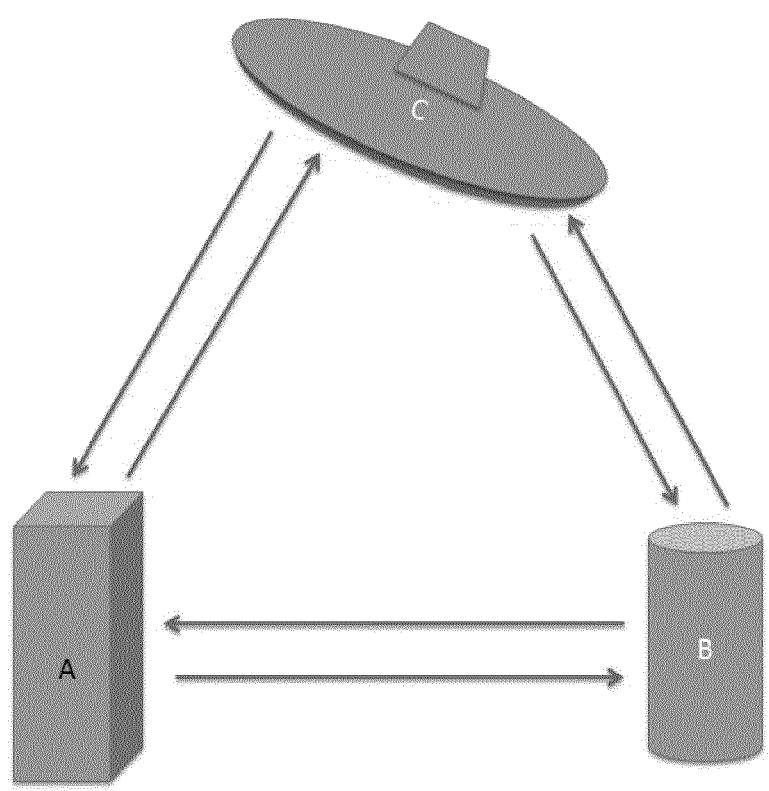
FIG. 2 shows a schematic representation of an operation room light communication system according to the invention comprising three units.

FIG. 2 shows a schematic view of an embodiment of an operation room light communication system according to the invention. In this embodiment the communication system comprises three elements A, B and C. Other embodiments may comprise only two elements or more than three elements.

In the illustrated embodiment element C is an OR surgical light which is designed on the one hand as a surgical light and on the other hand as the central element of the optical communication system. It is provided with optical transmitters and receivers. It transmits data to and receives data from two devices A and B as it is shown by arrows in FIG. 2. The devices are provided with optical transmitters and receivers. They are able to directly communicate with each other, as it is further shown by arrows in FIG. 2. This direct communication may be effected optically, as well. Preferably the transmission frequency of this direct communication is selected in the infrared light range. The devices A and B may e.g. be patient monitors, endoscopic devices, an anesthesia ventilator, etc. The invention is not restricted to the surgical light C being the central element. Any element A, B or another additional element can be provided as the central or master element.

Figure 3:
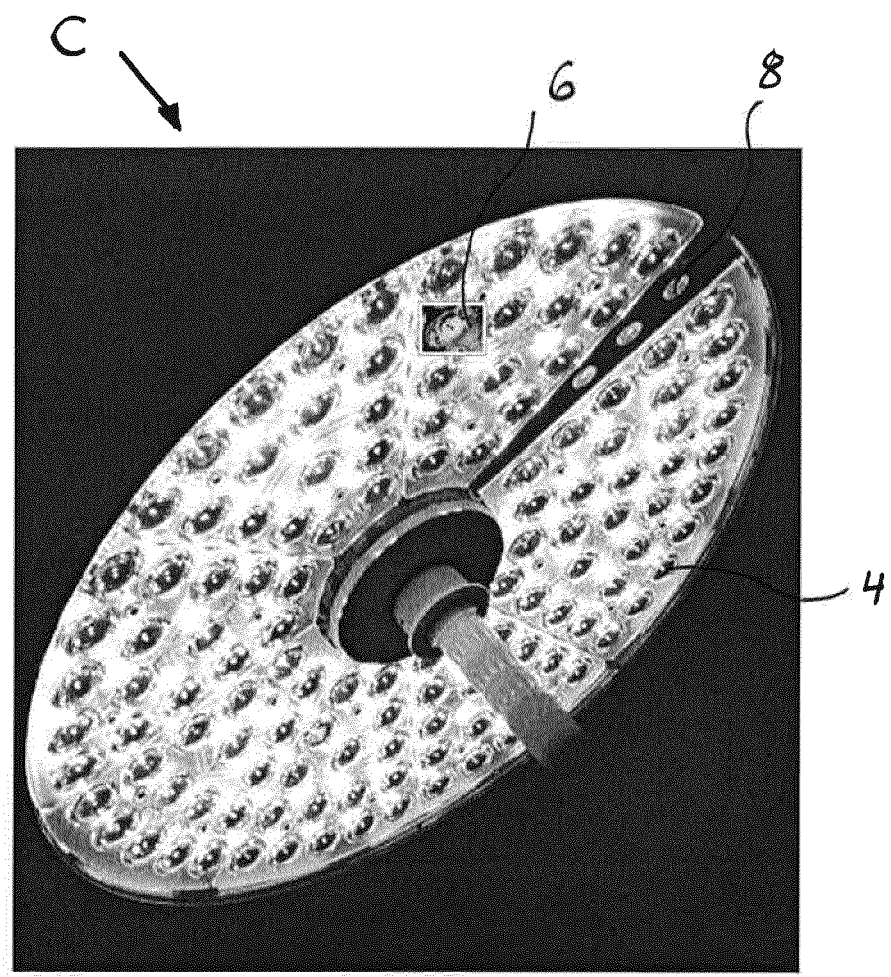
FIG. 3 shows a surgical OR light equipped with LEDs according to the invention.

The OR lamp C may comprise all or part of the control elements of the system. The control elements may also or additionally be provided in an extra device. In this embodiment the OR lamp C is on the one hand designed as a conventional LED OR lamp having a plurality of LEDs 4 and one or more LEDs 6 for providing the required illumination in the operation room, as it is shown in FIG. 3.

The LED 6 is provided with further functions. It is connected to a data source and/or a control unit the output of which is used to modulate the light emitted from LED 6. The modulation frequency is selected sufficiently high so that no light flickering is observed by the persons in the operation room. Unit 8 is provided for receiving optical data from the devices A and B, respectively.

The invention claimed is:

1. Operating room system including at least a first device and a second device, wherein the first device is provided with means for emitting and for receiving light signals and the second device is provided with means for receiving and emitting light signals, wherein the light signals are transferred in an exclusively wireless manner between the first device and the second device and carry information which information is modulated into the light signals, the first device is a lighting device, the second device is a medical instrument, wherein the first device exclusively transfers the control signals of the second device to the second device and wherein all output information from the second device is transferred by means of light signals in a wireless manner to the first device, control means are provided in the operating room system for managing communication access between the two devices including a hierarchy priority decision means for the data exchange between the first device and the second device.

2. Operating room system according to claim 1, wherein the light is visible light.

3. Operating room system according to claim 1 wherein the light is infrared light.

4. Operating room system according to claim 1, wherein the lighting device comprises at least one light emitting diode or laser diode and wherein the intensity of the light emitted by the light emitting diode or laser diode is modulated.

5. Operating room system according to claim 1, comprising further devices provided with means for emitting and for receiving light signals carrying information which information is modulated into the light signals, respectively, wherein the communication managing control means includes means for adjusting the bandwidth for communication between each two devices exchanging light signals and the hierarchy priority decision means for the data exchange between the devices is provided with a decision means deciding on the respective communication access of two devices and includes switching means for switching the communication access to the devices with the highest priority.

6. Operation room system according to claim 1, comprising adjustment means for adjusting signals sent and received from devices to detect and improve quality reducing jitter and other communication impurities that otherwise cause the signals to be of poor quality.

7. Operation room system according to claim 1, wherein a base station is provided which comprises the control means.

8. Operation room system according to claim 7, wherein the base station is provided for receiving and transmitting analog signals.

9. Operation room system according to claim 7, wherein the lighting device communicates with the base station.

10. Operation room system according to claim 1, wherein based on and representative of an analog signal a first digital signal is provided for transmission within the operation room system and further a second digital signal based upon the first digital signal is produced for other communication services.

11. Operation room system according to claim 1, wherein based on and representative of a first digital signal an analog signal based on the first digital signal is produced for communication with analog signal receivers.

12. Operation room system according to claim 1, wherein at least one device is configured to receive a signal from a base station of the network.

13. Operation room system according to claim 12, wherein at least one device is configured to emit a signal to the base station of the network.

14. Operation room system according to claim 1, wherein a device is configured to receive a further light signal comprising a further operation room device signal from each of one or more operation room devices, and to produce a further analog signal based upon the further light signal, wherein the further analog signal is for transmission to a base station of an operating room network.

15. Operation room system according to claim 14, wherein the further light signal has different wavelengths from the light output by the light source.

16. Operation room system according to claim 1, wherein the medical instrument comprises a minimally invasive instrument.

17. A method for sending and receiving data in an operation room system, wherein
- light is exclusively used in an exclusively wireless manner for transferring signals between the devices of the system, the light carrying information which information is modulated into the light signals,
- the light is emitted from a lighting device to a medical instrument, in particular, but not exclusively a minimally invasive instrument,
- the light exclusively transfers control signals to the medical instrument and wherein all output information from the medical instrument is transferred by means of light signals in a wireless manner to the lighting device,
- communication access between the lighting device and the medical instrument is managed, including performing hierarchy priority decisions for the data exchange between the lighting device and the medical instrument.

18. The method of claim 17, wherein digital traffic control processing is executed with respect to the sending and receiving of data.

19. The method of claim 17, wherein data are sent and received between the aforesaid and/or further devices of the operation system device.

\* \* \* \* \*